United States Patent
König et al.

(10) Patent No.: US 9,309,270 B2
(45) Date of Patent: Apr. 12, 2016

(54) PROCESS FOR THE SILYLATION OF 2-AMINO-1,3,5-TRIAZINES

(71) Applicant: BASF SE, Ludwigshafen (DE)

(72) Inventors: Alexander König, Bruchsal (DE); Rebekka Von Benten, Ludwigshafen (DE); Jens Aβmann, Neustadt (DE); Edwin Kroke, Halsbruecker (DE); Sandra Jähnigen, Freiberg (DE); Anke Schwarzer, Freiberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/782,098

(22) PCT Filed: Apr. 1, 2014

(86) PCT No.: PCT/EP2014/056494
§ 371 (c)(1),
(2) Date: Oct. 2, 2015

(87) PCT Pub. No.: WO2014/161834
PCT Pub. Date: Oct. 9, 2014

(65) Prior Publication Data
US 2016/0052945 A1    Feb. 25, 2016

(30) Foreign Application Priority Data
Apr. 5, 2013 (EP) .................. 13162435

(51) Int. Cl.
C07F 7/10 (2006.01)
C07D 251/42 (2006.01)
C07D 251/48 (2006.01)
C07D 251/54 (2006.01)

(52) U.S. Cl.
CPC .................. *C07F 7/10* (2013.01)

(58) Field of Classification Search
CPC .................. C07F 7/10
USPC .................. 544/194, 180
See application file for complete search history.

(56) References Cited

FOREIGN PATENT DOCUMENTS

DE    2208329 A1    9/1972

OTHER PUBLICATIONS

International Search Report for PCT/EP2014/056494 mailed Jul. 7, 2014.

*Primary Examiner* — Venkataraman Balasubramanian
(74) *Attorney, Agent, or Firm* — Drinker Biddle & Reath LLP

(57) ABSTRACT

The present invention relates to a method for silylating 2-amino-1,3,5-triazines of the general formula (I)

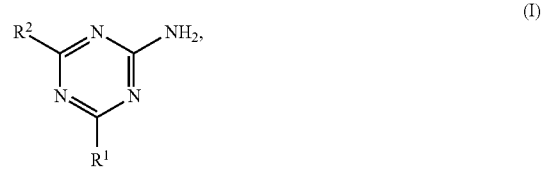

in which
$R^1$ and $R^2$ are each independently hydrogen, hydroxyl, $NH_2$, $NHR^3$, $NR^3_2$, $NO_2$, $NHCOR^3$, $C_1$- to $C_2$-alkyl, $C_1$- to $C_{20}$-hydroxyalkyl, $C_2$- to $C_{20}$-alkenyl, $C_1$- to $C_{20}$-alkoxy, aryl or aryloxy optionally substituted with $C_1$- to $C_8$-alkyl and
$R^3$ is $C_1$- to $C_{20}$-alkyl, $C_3$- to $C_{12}$-cycloalkyl, $C_4$ to $C_{30}$-alkylcycloalkyl, aryl optionally substituted with $C_1$- to $C_8$-alkyl,
with silanes, by reacting silanes of the general formula (II)

$$X{-}SiH(R^4R^5) \qquad (II),$$

in which
X is fluorine, chlorine, bromine or iodine
$R^4$ and $R^5$ are each independently $C_1$- to $C_{20}$-alkyl, $C_1$- to $C_{20}$-hydroxyalkyl, $C_1$- to $C_{20}$-haloalkyl, $C_2$- to $C_{20}$-alkenyl, $C_1$- to $C_{20}$-alkoxy, aryl or aryloxy optionally substituted with $C_1$- to $C_8$-alkyl, in the presence of a base.

19 Claims, No Drawings

PROCESS FOR THE SILYLATION OF 2-AMINO-1,3,5-TRIAZINES

CROSS-REFERENCE TO RELATED APPLICATIONS

This application is a national stage application (under 35 U.S.C. §371) of PCT/EP2014/056494, filed Apr. 1, 2014, which claims benefit of European Application No. 13162435.5, filed Apr. 5, 2013, both of which are incorporated herein by reference in their entirety.

The present invention relates to a method for silylating 2-amino-1,3,5-triazines by reacting 2-amino-1,3,5-triazines with specific silanes in the presence of a base.

BACKGROUND OF THE INVENTION

A two-stage process for the complete silylation of melamine or 2,4-diamino-6-phenyl-1,3,5-triazine a) by reaction with trimethylchlorosilane and triethylamine and b) by reaction with butyllithium and dimethylchlorosilane is known from Inorganic Chemistry Communications, 2002, 5(7), pages 516 to 518. For melamine, this process leads to a yield of 58% in the first stage and to a yield of 55% in the second stage, resulting in an overall yield of ca. 32%. In the case of 2,4-diamino-6-phenyl-1,3,5-triazine, this process leads to a yield of 84% in the first stage and to a yield of 87% in the second stage, resulting in an overall yield of ca. 73%. The yields for both the partial and for the complete silylation are unsatisfactory.

Zhurnal Obshchei Khimii 49(5), 1057-60 (1979) report heating melamine and tetramethyldisilazane $(Me_2HSi)_2NH$ at 110 to 140° C. for 8h in the presence of ammonium sulfate. This leads to various mixtures of N-bridged $SiMe_2H$ triazines in yields of 72.5%. The yield of the silylation is unsatisfactory.

The object of the present invention was therefore to overcome the abovementioned disadvantages.

DETAILED DESCRIPTION OF THE INVENTION

Accordingly, a novel and improved method has been found for silylating 2-amino-1,3,5-triazines of the general formula (I)

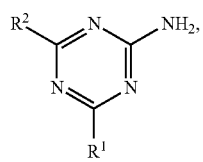
(I)

in which $R^1$ and $R^2$ are each independently hydrogen, hydroxyl, $NH_2$, $NHR^3$, $NR^3_2$, $NO_2$, $NHCOR^3$, $C_1$- to $C_2$-alkyl, $C_1$- to $C_{20}$-hydroxyalkyl, $C_2$- to $C_{20}$-alkenyl, $C_1$- to $C_{20}$-alkoxy, aryl or aryloxy optionally substituted with $C_1$- to $C_8$-alkyl and $R^3$ is $C_1$- to $C_{20}$-alkyl, $C_3$- to $C_{12}$-cycloalkyl, $C_4$ to $C_{30}$-alkylcycloalkyl, aryl optionally substituted with $C_1$- to $C_8$-alkyl, with silanes, wherein silanes of the general formula (II)

(II), in which

X is fluorine, chlorine, bromine or iodine $R^4$ and $R^5$ are each independently $C_1$- to $C_{20}$-alkyl, $C_1$- to $C_{20}$-hydroxyalkyl, $C_1$- to $C_{20}$-haloalkyl, $C_2$- to $C_{20}$-alkenyl, $C_1$- to $C_{20}$-alkoxy, aryl or aryloxy optionally substituted with $C_1$- to $C_8$-alkyl, are reacted in the presence of a base.

The residues/substituents of the 2-amino-1,3,5-triazines of the general formula (I) and of the silanes of the general formula (II) are given below:

$R^1$, $R^2$, $R^3$, $R^4$, $R^5$, each independently $C_1$- to $C_{20}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec-butyl and tert-butyl, particularly methyl and ethyl, $R^1$, $R^2$, $R^3$, $R^4$ and $R^5$ each independently aryl optionally substituted with $C_1$- to $C_8$-alkyl, preferably aryl optionally mono- to trisubstituted with $C_1$- to $C_4$-alkyl, such as phenyl, 1-naphthyl, 2-naphthyl, o-methylphenyl, m-methylphenyl, p-methylphenyl, o-/p-dimethylphenyl, particularly preferably phenyl optionally mono- or disubstituted with $C_1$- to $C_2$-alkyl, such as phenyl, o-methylphenyl, m-methylphenyl, p-methylphenyl, o-/p-dimethylphenyl.

$R^4$ and $R^5$ each independently $C_1$- to $C_{20}$-haloalkyl, preferably $C_1$- to $C_8$-haloalkyl, particularly preferably $C_1$- to $C_4$-haloalkyl, such as fluoromethyl, difluoromethyl, trifluoromethyl, chloromethyl, dichloromethyl, trichloromethyl, bromomethyl, dibromomethyl, tribromomethyl, iodomethyl, particularly chloromethyl, dichloromethyl and trichloromethyl.

$R^1$, $R^2$, $R^4$, $R^5$, $R^6$, $R^7$, $R^8$, $R^9$, $R^{10}$, $R^{11}$, $R^{12}$ and $R^{13}$ each independently hydrogen, with the proviso that $R^6$, $R^7$ and $R^8$ are not simultaneously hydrogen, $R^1$ and $R^2$ each independently hydroxyl,
$NH_2$,
$NHR^3$,
$NR^3_2$,
$NO_2$,
$NHCOR^3$, $R^1$, $R^2$, $R^4$ and $R^5$ each independently $C_1$- to $C_{20}$-hydroxyalkyl, preferably $C_1$- to $C_8$-hydroxyalkyl, particularly preferably $C_1$- to $C_4$-hydroxyalkyl, such as hydroxymethyl, hydroxyethyl and hydroxypropyl, particularly hydroxymethyl and hydroxyethyl, $C_1$- to $C_{20}$-alkenyl, preferably $C_2$- to $C_8$-alkenyl, particularly preferably $C_2$- to $C_4$-alkenyl, such as ethenyl, propenyl and butenyl, particularly 1-ethenyl, $C_1$- to $C_{20}$-alkoxy, preferably $C_1$- to $C_8$-alkoxy, particularly preferably $C_1$- to $C_4$-alkoxy, such as methoxy, ethoxy, n-propoxy, isopropoxy, n-butoxy, isobutoxy and sec-butoxy, particularly methoxy and ethoxy, aryloxy optionally substituted with $C_1$- to $C_8$-alkyl, preferably aryloxy optionally mono- to trisubstituted with $C_1$- to $C_4$-alkyl, such as phenoxy, 1-naphthoxy, 2-naphthoxy, o-methylphenoxy, m-methylphenoxy, p-methylphenoxy and o-/p-dimethylphenoxy, particularly preferably phenoxy optionally mono- or disubstituted with $C_1$- to $C_2$-alkyl, such as phenoxy, o-methylphenoxy, m-methylphenoxy, p-methylphenoxy and o-/p-dimethylphenoxy, $R^3$ $C_3$- to $C_{12}$-cycloalkyl such as cyclopropyl, cyclobutyl, cyclopentyl, cyclohexyl, cycloheptyl, cyclooctyl, cyclononyl, cyclodecyl, cycloundecyl and cyclodocecyl, preferably $C_3$- to $C_8$-cycloalkyl such as cyclopropyl, cyclobutyl, cyclopentyl, cyclohexyl, cycloheptyl and cyclooctyl, preferably $C_5$-, $C_6$- and $C_8$-cycloalkyl such as cyclopentyl, cyclohexyl and cyclooctyl, cycloalkyl substituted with $C_1$- to $C_8$-alkyl, particularly preferably $C_3$- to $C_8$-cycloalkyl substituted with $C_1$- to $C_8$-alkyl, such as 2-methylcyclopentyl and 2-methylcyclohexyl, $R^6$, $R^7$, $R^8$, $R^9$, $R^{10}$, $R^{11}$, $R^{12}$ and $R^{13}$ each independently $C_1$- to $C_{10}$-alkyl, preferably $C_1$- to $C_8$-alkyl, particularly preferably $C_1$- to $C_4$-alkyl, such as methyl, ethyl, n-propyl, isopropyl, n-butyl, isobutyl, sec-butyl and tert-butyl, particularly methyl and ethyl, $R^6$, $R^7$ and $R^8$ together
=$CR^9$—$CR^{10}$=$CR^{11}$—$CR^{12}$=$CR^{13}$— or
=$CR^9$—NH—$CR^{10}$=$CR^{11}$—.

The method according to the invention may be carried out as follows:

The 2-amino-1,3,5-triazines (I) and the solvent may be charged simultaneously or in any sequence, the base is added and then the compounds (II). The combining of the reaction mixture may generally be carried out at temperatures of (−5) to 30° C., preferably 5 to 25° C., particularly preferably 10 to 25° C., particularly room temperature, the addition of the base preferably at (−5) to 10° C., particularly preferably 0 to 5° C., and at a pressure of 0.01 to 10 bar, preferably 0.1 to 2 bar, preferably standard pressure (atmospheric pressure). The reaction may generally be carried out at temperatures of 35 to 110° C., preferably 50 to 90° C., particularly preferably 67 to 81° C., particularly under reflux and at a pressure of 0.01 to 10 bar, preferably 0.1 to 2 bar, preferably standard pressure (atmospheric pressure).

Suitable 2-amino-1,3,5-triazines of the general formula (I) are melamine (2,4,6-triamino-1,3,5-triazine), ammeline (4,6-diamino-2-hydroxy-1,3,5-triazine), ammelide (6-amino-2,4-dihydroxy-1,3,5-triazine), 2-amino-1,3,5-triazine, 2-substituted 4,6-diamino-1,3,5-triazines, 2-substituted 4-amino-6-hydroxy-1,3,5-triazines, melam (N2-[4,6-diamino-1,3,5-triazin-2-yl]-1,3,5-triazine-2,4,6-triamine).

Suitable silanes of the general formula (II) are diorganohalosilanes, for example dialkylhalosilanes, diarylhalosilanes and diorganochlorosilanes such as dimethylhalosilanes, diethylhalosilanes, dipropylhalosilanes, dibutylhalosilanes, diphenylhalosilanes, dimethylchlorosilanes, diethylchlorosilanes, dipropylchlorosilanes, dibutylchlorosilanes, diphenylchlorosilanes, diethylbromosilane, dipropylbromosilane and dibutylchlorosilane, preferably diorganochlorosilane and diorganobromosilane such as dimethylchlorosilane, diethylchlorosilane, dipropylchlorosilane, dibutylchlorosilane, diphenylchlorosilane, diethylbromosilane, dipropylbromosilane and dibutylchlorosilane, particularly preferably dimethylchlorosilane, diethylchlorosilane, diphenylchlorosilane and diethylbromosilane.

Suitable bases are primary, secondary and tertiary and also heterocyclic, aromatic amines of the general formula (III), $NR^6R^7R^8$ (III), in which
$R^6$, $R^7$, $R^8$ are each independently hydrogen or $C_1$- to $C_{10}$-alkyl, with the proviso that $R^6$, $R^7$ and $R^8$ are not simultaneously hydrogen, or are together =$CR^9$—$CR^{10}$=$CR^{11}$—$CR^{12}$=$CR^{13}$— or =$CR^9$—NH—$CR^{10}$=$CR^{11}$—,
$R^9$, $R^{10}$, $R^{11}$, $R^{12}$ and $R^{13}$ are each independently hydrogen or $C_1$- to $C_{10}$-alkyl, particularly methylamine, dimethylamine, trimethylamine, ethylamine, diethylamine, triethylamine, methylethylamine, ethyldimethylamine, methyldiethylamine, pyridine, 4-methylpyridine, imidazole and N-methylimidazole, preferably diethylamine, triethylamine, pyridine, particularly preferably triethylamine and pyridine.

The molar ratio of silane of the general formula (II) to the 2-amino-1,3,5-triazines of the general formula (I) is generally 12:1 to 6:1, preferably 10:1 to 6:1, particularly preferably 9:1 to 6:1.

The molar ratio of the base to the silane of the general formula (II) is generally 1.2:1 to 0.5:1, preferably 1:1 to 0.5:1, particularly preferably 1:1 to 0.75:1.

The molar ratio of the base to the 2-amino-1,3,5-triazines of the general formula (I) is generally 12:1 to 6:1, preferably 9:1 to 6:1, particularly preferably 7.5:1 to 6:1.

The silylated 2-amino-1,3,5-triazines of the general formula (I) are suitable as intermediates for flame retardants, melamine resins (sizes, impregnating resins, foams) or precursors for hard substance syntheses such as carbonitrides and catalytically active graphitic carbon nitrides or C/N/H materials and/or multinary carbide nitrides.

EXAMPLES

Example 1

Preparation of
2,4,6-tris(tetramethyldisilazyl)-1,3,5-triazine 10 g (79 mmol) of melamine were charged under an argon atmosphere in a 0.5 liter glass flask which was evacuated and flushed with argon three times, 300 ml of acetonitrile were added, the flask was cooled to 0 to 5° C., 80.95 g (800 mmol) of triethylamine were added and 75.7 g (800 mmol) of dimethylchlorosilane were added dropwise over a period of 40 min, the mixture was heated under reflux for 15 h and the solid was removed after cooling by means of a Schlenk frit. The filtrate was concentrated under reduced pressure, taken up in 100 ml of n-hexane, the precipitated solid was again filtered off and the filtrate was freed from n-hexane under reduced pressure. 33.77 g (97%) of 2,4,6-tris(tetramethyldisilazyl)-1,3,5-triazine were obtained with a purity of 90% with 10% of the NH functions not silylated.

$^1$H NMR [$CDCl_3$]: 0.41, 0.46 ppm ($CH_3$); 4.35 ppm (NH); 4.78, 4.84 ppm (Si—H).
$^{13}$C NMR [$CDCl_3$]: −1.8, 0.4 ppm ($CH_3$); 167.2, 170.4, 170.8 (triazine N)
$^{29}$Si NMR [$CDCl_3$]: −9.8, −12.0 ppm (Si)

Example 2

Preparation of N2-[4,6-di(tetramethyldisilazyl)-1,3,5-triazin-2-yl]-1,3,5-triazine-2,4,6-triamine 3 g (11.9 mmol) of melam were charged in a 0.25 liter glass flask under an argon atmosphere which was evacuated three times and flushed each time with argon, 150 ml of tetrahydrofuran were added, the flask was cooled to 0 to 5° C., 10.84 g (10.7 mmol) of triethylamine were added and 10.1 g (10.7 mmol) of dimethylchlorosilane were added dropwise over a period of 40 min, the mixture was heated under reflux for 15 h and the solid was removed after cooling by means of a Schlenk frit. The filtrate was concentrated under reduced pressure, taken up in 70 ml of n-hexane, the precipitated solid was again filtered off and the filtrate was freed from n-hexane under reduced pressure.

The highly viscous product was taken up again in 250 ml of tetrahydrofuran, 10.84 g (10.7 mmol) of triethylamine and 10.1 g (10.7 mmol) of dimethylchlorosilane were added, the mixture was heated under reflux for 8 h and the solid was removed after cooling by means of a Schlenk frit. The filtrate was concentrated analogously under reduced pressure, taken up in 70 ml of n-hexane, the solid was filtered off and the filtrate was freed from n-hexane under reduced pressure.

7.89 g (94%) of N2-[4,6-di(tetramethyldisilazyl)-1,3,5-triazin-2-yl]-1,3,5-triazine-2,4,6-triamine was obtained with few NH functions still present.

$^1$H NMR [CDCl$_3$]: 0.18-0.42 ppm (CH$_3$); 4.61-4.88 ppm (NH, Si—H).

$^{13}$C NMR [CDCl$_3$]: −1.0-1.2 ppm (CH$_3$); 167.1-171.0 ppm (triazine N)

$^{29}$Si NMR [CDCl$_3$]: −4.3, −11.3 ppm (Si)

The invention claimed is:

1. A method comprising silylating 2-amino-1,3,5-triazines of general formula (I) with silanes in the presence of a base to form a reaction mixture

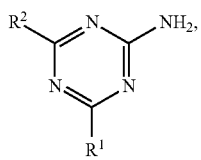
(I)

in which
R$^1$ and R$^2$ are each independently hydrogen, hydroxyl, NH$_2$, NHR$^3$, NR$^3{}_2$, NO$_2$, NHCOR$^3$, C$_1$- to C$_2$-alkyl, C$_1$- to C$_{20}$-hydroxyalkyl, C$_2$- to C$_{20}$-alkenyl, C$_1$- to C$_{20}$-alkoxy, aryl or aryloxy optionally substituted with C$_1$- to C$_8$-alkyl, and
R$^3$ is C$_1$- to C$_{20}$-alkyl, C$_3$- to C$_{12}$-cycloalkyl, C$_4$ to C$_{30}$-alkylcycloalkyl, aryl optionally substituted with C$_1$- to C$_8$-alkyl,
and the silanes are of general formula (II)

in which
X is fluorine, chlorine, bromine or iodine, and
R$^4$ and R$^5$ are each independently C$_1$- to C$_{20}$-alkyl, C$_1$- to C$_{20}$-hydroxyalkyl, C$_1$- to C$_{20}$-haloalkyl, C$_2$- to C$_{20}$-alkenyl, C$_1$- to C$_{20}$-alkoxy, aryl or aryloxy optionally substituted with C$_1$- to C$_8$-alkyl.

2. The method for silylating 2-amino-1,3,5-triazines according to claim 1, wherein
R$^1$ and R$^2$ are each independently hydrogen, hydroxyl, NH$_2$, NHR$^3$, NR$^3{}_2$, NO$_2$, NHCOR$^3$, C$_1$- to C$_8$-alkyl, C$_1$- to C$_8$-hydroxyalkyl, C$_2$- to C$_8$-alkenyl, C$_1$- to C$_8$-alkoxy, phenyl or phenoxy optionally substituted with C$_1$- to C$_4$-alkyl, and
R$^3$ is C$_1$- to C$_8$-alkyl, C$_3$- to C$_8$-cycloalkyl, C$_4$- to C$_{12}$-alkylcycloalkyl, phenyl optionally substituted with C$_1$- to C$_4$-alkyl.

3. The method for silylating 2-amino-1,3,5-triazines according to claim 1, wherein primary, secondary and tertiary and also heterocyclic, aromatic amines of general formula (III) are used as the base

in which
R$^6$, R$^7$, R$^8$ are each independently hydrogen or C$_1$- to C$_{10}$-alkyl, with the proviso that R$^6$, R$^7$ and R$^8$ are not simultaneously hydrogen, or are together =CR$^9$—CR$^{10}$=CR$^{11}$—CR$^{12}$=CR$^{13}$— or =CR$^9$—NH—CR$^{10}$=CR$^{11}$—, R$^9$, R$^{10}$, R$^{11}$, R$^{12}$ and R$^{13}$ are each independently hydrogen or C$_1$- to C$_{10}$-alkyl.

4. The method for silylating 2-amino-1,3,5-triazines according to claim 1, wherein the 2-amino-1,3,5-triazines (I) and solvent are charged simultaneously or in any sequence and the base and subsequently the silane is added.

5. The method for silylating 2-amino-1,3,5-triazines according to claim 1, wherein the reaction mixture is formed at temperatures of (−5) to 30° C.

6. The method for silylating 2-amino-1,3,5-triazines according to claim 1, wherein the base is added at a temperature of (−5) to 10° C.

7. The method for silylating 2-amino-1,3,5-triazines according to claim 1, wherein the silylation reaction is conducted at temperatures of 35 to 110° C.

8. The method for silylating 2-amino-1,3,5-triazines according to claim 1, wherein the silylation reaction is conducted under reflux.

9. The method for silylating 2-amino-1,3,5-triazines according to claim 1, wherein the silylation reaction is conducted at a pressure of 0.01 to 10 bar.

10. The method for silylating 2-amino-1,3,5-triazines according to claim 1, wherein a molar ratio of silane (II) to the 2-amino-1,3,5-triazines (I) is 12:1 to 6:1.

11. The method for silylating 2-amino-1,3,5-triazines according to claim 1, wherein the molar ratio of the base to the 2-amino-1,3,5-triazines (I) is 12:1 to 6:1.

12. The method for silylating 2-amino-1,3,5-triazines according to claim 1, wherein the 2-amino-1,3,5-triazines of the general formula (I) is a compound selected from the group consisting of melamine (2,4,6-triamino-1,3,5-triazine), ammeline (4,6-diamino-2-hydroxy-1,3,5-triazine), ammelide (6-amino-2,4-dihydroxy-1,3,5-triazine), 2-amino-1,3,5-triazine, 2-substituted 4,6-diamino-1,3,5-triazines, 2-substituted 4-amino-6-hydroxy-1,3,5-triazines, and melam (N2-[4,6-diamino-1,3,5-triazin-2-yl]-1,3,5-triazine-2,4,6-triamine).

13. The method for silylating 2-amino-1,3,5-triazines according to claim 1, wherein the silanes are diorganohalosilanes.

14. The method for silylating 2-amino-1,3,5-triazines according to claim 13, wherein the silanes are selected from dialkylhalosilanes, diarylhalosilanes and or diorganochlorosilanes.

15. The method for silylating 2-amino-1,3,5-triazines according to claim 13, wherein the silanes of the general formula (II) are selected from the group consisting of dimethylhalosilanes, diethylhalosilanes, dipropylhalosilanes, dibutylhalosilanes, diphenylhalosilanes, dimethylchlorosilanes, diethylchlorosilanes, dipropylchlorosilanes, dibutylchlorosilanes, diphenylchlorosilanes, diethylbromosilane, dipropylbromosilane and dibutylchlorosilane.

16. The method for silylating 2-amino-1,3,5-triazines according to claim 13, wherein the silanes of the general formula (II) used are diorganochlorosilanes or diorganobromosilanes selected from dimethylchlorosilanes, diethylchlorosilanes, dipropylchlorosilanes, dibutylchlorosilanes, diphenylchlorosilanes, diethylbromosilane, dipropylbromosilane or dibutylchlorosilane.

17. The method for silylating 2-amino-1,3,5-triazines according to claim 13, wherein the silanes are selected from dimethylchlorosilane, diethylchlorosilane, diphenylchlorosilane or diethylbromosilane.

18. The method for silylating 2-amino-1,3,5-triazines according to claim 1, wherein the base is selected from the group consisting of methylamine, dimethylamine, trimethylamine, ethylamine, diethylamine, triethylamine, methylethylamine, ethyldimethylamine, methyldiethylamine, pyridine, 4-methylpyridine, imidazole, N-methylimidazole and mixtures thereof.

19. The method for silylating 2-amino-1,3,5-triazines according to claim 18, wherein the silanes of the general formula (II) are selected from the group consisting of dimethylhalosilanes, diethylhalosilanes, dipropylhalosilanes, dibutylhalosilanes, diphenylhalosilanes, dimethylchlorosilanes, diethylchlorosilanes, dipropyichlorosilanes, dibutylchlorosilanes, diphenylchlorosilanes, diethylbromosilane, dipropylbromosilane and dibutylchlorosilane.

* * * * *